US006150333A

United States Patent [19]
Moreau

[11] Patent Number: 6,150,333
[45] Date of Patent: *Nov. 21, 2000

[54] METHODS OF USING A SOMATOSTATIN ANALOGUE

[75] Inventor: Jacques-Pierre Moreau, Upton, Mass.

[73] Assignee: Biomeasure, Inc., Milford, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 09/361,394

[22] Filed: Jul. 26, 1999

Related U.S. Application Data

[60] Provisional application No. 60/094,693, Jul. 30, 1998.

[51] Int. Cl.$^7$ .................................................. A61K 38/00
[52] U.S. Cl. ............................................................... 514/16
[58] Field of Search ................................................ 514/16

[56] References Cited

U.S. PATENT DOCUMENTS

| | | |
|---|---|---|
| 4,853,371 | 8/1989 | Coy et al. . |
| 5,073,541 | 12/1991 | Taylor et al. . |
| 5,147,856 | 9/1992 | Ramwell et al. . |
| 5,411,943 | 5/1995 | Bogden . |
| 5,504,069 | 4/1996 | Bogden et al. . |
| 5,686,418 | 11/1997 | Culler . |

FOREIGN PATENT DOCUMENTS

| | | |
|---|---|---|
| WO 98/08528 | 3/1998 | WIPO . |
| WO 98/08529 | 3/1998 | WIPO . |
| WO 98/10786 | 3/1998 | WIPO . |
| WO 98/51332 | 11/1998 | WIPO . |

OTHER PUBLICATIONS

Anthony et al.,"Case Report: Lanreotide in the Management of Hypercalcemia of Malignancy," *American Journal of the Medical Sciences*, vol. 309, No. 6, Jun. 1995, pp. 312–314.
Kirk et al., "Somatostatin analogue in short term management of hyperinsulinism",*Archives of Disease in Childhood*, vol. 63, No. 12, 1988, pp. 1493–1494.
Khoo et al., "Palliation of malignant intestinal obstruction using ocreotide," *Eurpoean Journal of Cancer*,vol. 30A, No. 1, 1994,pp. 28–30.
Lamrani et al., "Effects of lanreotide, a somatostatin. . . secretions in humans," *British Journal of Clinical Pharmacology*,vol. 43, No. 1, 1997, pp. 65–70.
Clark, R.V., Clin. Res, vol. 38, No. 4, p. 943A, 1990.
Ambrosi, B., Acta Endocrinologica, vol. 122, pp. 569–576, 1990.
Palmieri, G.M.A., J. Bone and Mineral Research, vol. 7, Sup. 1, (Abs. 591) p. S240, 1992.
Koberstein, B., et al., Z. Gastroenterol, vol. 28, pp. 295–301, 1990.
Christensen, C., Acta Chir Scand., vol. 155, pp. 541–543, 1989.
Laron, Z., Israel J. Med. Sci., vol. 26, pp. 1–2, 1990.
Wilson, D., et al., Irish J. of Med. Sci., vol. 158, No. 1, pp. 31–32, 1989.

Micic, D., et al., Digestion, vol. 16, Sup. 1, p. 70, Abs. 193, 1990.
Mozell, E., et al., Surg., Gyn. & Obstetrics, vol. 170, pp. 476–484, 1990.
Cello, J.P., et al., Gastroenterol., vol. 98, No. 5 Pt.2, p. A163, 1990.
Alhindawi, R., et al., Canada J. Surg., vol. 33, No. 2, pp. 139–142, 1990.
Bianco, J. A., et al., Transplantation, vol. 49, No. 6, pp. 1194–1195, 1990.
O'Donnell, L.J.D., et al., Aliment. Pharmacol. Therap., vol. 4, No. 2, pp. 177–181, 1990.
Tulassay, Z., et al., Gastroenterology vol. 98, No. 5, Part 2, p. A238, 1990.
Fedorak, R.N., et al., Canada J. Gastroenterol, vol. 3, No. 2, pp. 53–57, 1989.
Modigliani, E., et al., Annales d'Endocrinologie, vol. 50, p. 483–488, 1989.
Camisa, C., et al., Cleveland Clinic J. Medicine, vol. 57, No. 1, pp. 71–76, 1990.
Hoeldtke, R.D., et al., Arch Phys Med Rehabil., vol. 69, pp. 895–898, 1988.
Kooner, J.S., et al., Proceedings of the Brit J. Clin. Pharm., vol. 28, pp. 735P–736P, Jul. 12–14, 1989.
Abelson, J.L., et al., J. Clinical Psychopharmacol, vol. 10, No. 2, pp. 128–132. 1990.
Soudah, H., et al., Clin. Research, vol. 39, No. 2, p. 303A, 1991.
Nott, D.M., et al., Brit. J. Surg., vol. 77, p. A691, 1990.
Branch, M.S., Gastroenterol, vol. 100, No. 5 Pt. 2, p. A425, 1991.
Chang, T.C.,et al., Brit Med Journ, vol. 304, p. 158, 1992.
Prelevic, G.M., et al., Metabolism, vol. 41, No. 9, Sup. 2, pp. 76–79, 1992.
Jenkins, S.A., et al., Gut, vol. 33, pp. 404–407, 1992.
Arrigoni, A., et al., Amer. Journal Gastroenterol, vol. 87, p. 1311, abs. 275, 1992.
Hartley, J.E., et al., Journal Royal Soc. Med., vol. 85, pp. 107–108.
Koper, J.W., et al., Journal of Clinical Endo. and Metabolism, vol. 74, No. 3, pp. 543–547, 1992.
Bartlett, D.L., et al., Surgical Forum (Amer. Coll. Surg.), vol. 42, pp. 14–16, 1991.

(List continued on next page.)

*Primary Examiner*—Raymond Henley, III
*Attorney, Agent, or Firm*—John D. Conway; Brian R. Morrill; Fish & Richardson

[57] ABSTRACT

The present invention is directed to a method of treating one or more of the following disease and/or conditions, which comprises administering to a patient in need thereof the compound H-β-D-Nal-Cys-Tyr-D-Trp-Lys-Val-Cys-Thr-NH$_2$, where the Cysteines are bonded by a disulfide bond, or a pharmaceutically acceptable salt thereof, most preferably the acetate salt of the compound, in the treatment of certain diseases and/or conditions such as gastroenterological conditions and/or diseases, endocrinological diseases and/or conditions, various types of cancers and conditions associated with cancer such as cancer cachexia and in the treatment of hypotension and panic attacks.

4 Claims, No Drawings

OTHER PUBLICATIONS

Hasler, W., et al., Gastroenterol., vol. 100, No. 5 Pt.2, p. A428, 1991.

Soudah, H., et al., Gastroenterol., vol. 98, No. 5 Pt. 2, Suppl. A129, 1990.

Bauer, W., Europ J. Pharmacol, vol. 183, p. 55, 1990.

Petrelli, N., et al., Proc. Amer. Soc. Clin. Oncol., vol. 10, p. 138, 1991.

Miller, D., et al., Can Med Assoc J, 1991, vol. 145, No. 3, pp. 227–228.

Mosdell et al., "Emerging indications for ocreotide therapy, part 1,"*Am. J. Hosp. Pharm.*,vol. 51, No. 9, 1994, pp. 1184–1192.

Mottet, et al., "Hemodynamic Effects of the Somatostatin Analog . . . Echo–Doppler Study," *Hepatolgy*, vol. 27, No. 4, 1998, pp. 920–925.

Ono et al., "Effects of Ocreotide Acetate Treatment for Scleroderma Bowel," *Medical Journal,* vol. 22, No. 4, 1996, pp. 233–237.

Pavolovic et al.,"Regression of Sclerodermatous Skin Lesions in a Patient with Carcinoid Syndrome Treated by Octreotide," *Archives of Dermatology,*vol. 41, No. 2, pp. 1207–1209.

Sobhani et al.,"Lanreotide inhibits human jejunal secretion induced by prostaglandin E1 in healthy volunteers," *British Journal of Clinical Pharmacology,*vol. 41, No. 2, 1996, pp. 109–114.

Wecbecker et al.,"Somatostatin Analogs for Diagnosis and Treatment of Cancer," *Phamacology and Therapeutics* vol. 60, No. 2, 1994, pp. 245–264.

Woltering et al., "Detection of occult gastrinomas with iodine 125 labeled lanreotide and intraoperative gamma detection," *Surgery*vol. 116, No.6, 1994, pp. 1139–1147.

METHODS OF USING A SOMATOSTATIN ANALOGUE

CROSS-REFERENCE TO RELATED APPLICATION

This application is a non-provisional application claiming benefit of provisional application number 60/094,693, filed Jul. 30, 1998.

BACKGROUND OF THE INVENTION

The present invention is directed to a method of treating one or more of the following diseases and/or conditions in a patient in need thereof, which comprises the administration of the compound of the formula H-β-D-Nal-Cys-Tyr-D-Trp-Lys-Val-Cys-Thr-NH$_2$ (also known as lanreotide), where the two Cysteines are bonded by a disulfide bond, or a pharmaceutically acceptable salt thereof, most preferably the acetate salt of the compound, in the treatment of certain diseases and/or conditions such as gastroenterological conditions and/or diseases, such as Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, upper gastrointestinal bleeding, postprandial portal venous hypertension especially in cirrhotic patients, complications of portal hypertension, small bowel obstruction, gastroesophageal reflux, duodenogastric reflux and in treating endocrinological diseases and/or conditions, such as Cushing's Syndrome, gonadotropinoma, hyperparathyroidism, Graves' Disease, diabetic neuropathy, macular degeneration, hypercalcemia of malignancy, Paget's disease, and polycystic ovary disease; in treating various types of cancer such as thyroid cancer, leukemia, meningioma and conditions associated with cancer such as cancer cachexia; in the treatment of such conditions as hypotension such as orthostatic hypotension and postprandial hypotension and panic attacks.

Lanreotide is an analog of somatostatin and is known to inhibit growth hormone release as well as inhibit insulin, glucagon and pancreatic exocrine secretion.

U.S. Pat. No. 4,853,371 discloses lanreotide, a method for making it and a method for inhibiting the secretion of growth hormone, insulin, glucagon and pancreatic exocrine secretion.

U.S. Pat. No. 5,147,856 discloses the use of lanreotide of treating restenosis.

U.S. Pat. No. 5,411,943 discloses the use of lanreotide for treating hepatoma.

U.S. Pat. No. 5,073,541 discloses the use of lanreotide for treating lung cancer.

U.S. application Ser. No. 08/089,410 filed Jul. 9, 1993 discloses the use of lanreotide for treating melanoma.

U.S. Pat. No. 5,504,069 discloses the use of lanreotide for inhibiting the accelerated growth of a solid tumor.

U.S. application Ser. No. 08/854,941 filed May 13, 1997, discloses the use of lanreotide for decreasing body weight.

U.S. application Ser. No. 08/854,943 filed May 13, 1997, discloses the use of lanreotide for treating insulin resistance and Syndrome X.

U.S. Pat. No. 5,688,418 discloses the use of lanreotide for prolonging the survival of pancreatic cells.

PCT Application No. PCT/US97/14154 discloses the use of lanreotide for treating fibrosis.

U.S. application Ser. No. 08/855,311 filed May 13, 1997, discloses the use of lanreotide for treating hyperlipidemia.

U.S. application Ser. No. 08/440,061 filed May 12, 1995, discloses the use of lanreotide for treating hyperamylinemia.

U.S. application Ser. No. 08/852,221 filed May 7, 1997, discloses the use of lanreotide for treating hyperprolactinemia and prolactinomas.

The contents of the foregoing patents and applications are incorporated herein by reference.

SUMMARY OF THE INVENTION

This invention is directed to a method of treating a disease or condition which comprises administering to a patient in need thereof an effective amount of the compound H-β-D-Nal-Cys-Tyr-D-Trp-Lys-Val-Cys-Thr-NH$_2$, where the two Cysteines are bonded by a disulfide bond, or a pharmaceutically acceptable salt thereof, wherein the disease or condition is selected from the group consisting of systemic sclerosis, pancreatic pseudocysts, pancreatic ascites, VIPoma, nesidoblastosis, hyperinsulinism, gastrinoma, Zollinger-Ellison Syndrome, hypersecretory diarrhea, scleroderma, irritable bowel syndrome, upper gastrointestinal bleeding, postprandial portal venous hypertension, complications of portal hypertension, small bowel obstruction, duodenogastric reflux, Cushing's Syndrome, gonadotropinoma, hyperparathyroidism, diabetic neuropathy, macular degeneration, hypercalcemia of malignancy, Paget's disease, meningioma, cancer cachexia, psoriasis, hypotension and panic attacks.

A preferred method of the immediately foregoing method is where the acetate salt of H-β-D-Nal-Cys-Tyr-D-Trp-Lys-Val-Cys-Thr-NH$_2$ is administered.

A preferred method of the immediately foregoing method is where the disease or condition is selected from the group consisting of VIPoma, nesidoblastosis, hyperinsulinism, gastrinoma, hypersecretory diarrhea, irritable bowel syndrome, upper gastrointestinal bleeding, postprandial portal venous hypertension, especially in cirrhotic patients, complications of portal hypertension, small bowel obstruction, diabetic neuropathy, meningioma and cancer cachexia.

A preferred method of the immediately foregoing method is where the disease or condition treated is selected from the group consisting of VIPoma, nesidoblastosis, hypersecretory diarrhea, irritable bowel syndrome, small bowel obstruction and diabetic neuropathy.

In another aspect, the present invention is directed to a pharmaceutical composition comprising a pharmaceutically acceptable carrier and an effective amount of the acetate salt of H-β-D-Nal-Cys-Tyr-D-Trp-Lys-Val-Cys-Thr-NH$_2$ to treat a disease or condition wherein the disease or condition is selected from the group consisting of systemic sclerosis, pancreatic pseudocysts, pancreatic ascites, VIPoma, nesidoblastosis, hyperinsulinism, gastrinoma, Zollinger-Ellison Syndrome, hypersecretory diarrhea, scleroderma, irritable bowel syndrome, upper gastrointestinal bleeding, postprandial portal venous hypertension, especially in cirrhotic patients, complications of portal hypertension, small bowel obstruction, duodenogastric reflux, Cushing's Syndrome, gonadotropinoma, hyperparathyroidism, diabetic neuropathy, macular degeneration, hypercalcemia of malignancy, Paget's disease, meningioma, cancer cachexia, psoriasis, hypotension and panic attacks.

DETAILED DESCRIPTION

Lanreotide is readily prepared according to the procedure disclosed in U.S. Pat. No. 4,853,371, or the procedure disclosed in U.S. Pat. No. 5,411,943, the teachings of which are incorporated herein by reference. Lanreotide is currently marketed as the acetate salt in a 30 mg long-acting form and is available from Ipsen Biotech, Paris, France.

As is well known to those skilled in the art, the known and potential uses of somatostatin are varied and multitudinous. Somatostatin is known to be useful in the treatment of the diseases and/or conditions listed hereinbelow. The varied uses of somatostatin may be summarized as follows: Cushings Syndrome (see Clark, R. V. et al, Clin. Res. 38, p. 943A, 1990); gonadotropinoma (see Ambrosi B., et al., Acta Endocr. (Copenh.) 122, 569–576, 1990); hyperparathyroidism (see Miller, D., et al., Canad. Med. Ass. J., Vol. 145, pp. 227–228, 1991); Paget's disease (see, Palmieri, G. M. A., et al., J. of Bone and Mineral Research, 7, (Suppl. 1), p. S240 (Abs. 591), 1992); VIPoma (see Koberstein, B., et al., Z. Gastroenterology, 28, 295–301, 1990 and Christensen, C., Acta Chir. Scand. 155, 541–543, 1989); nesidioblastosis and hyperinsulinism (see Laron, Z., Israel J. Med. Sci., 26, No. 1, 1–2, 1990, Wilson, D. C., Irish J. Med. Sci., 158, No. 1, 31–32, 1989 and Micic, D., et al., Digestion, 16, Suppl. 1.70. Abs. 193, 1990); gastrinoma (see Bauer, F. E., et al., Europ. J. Pharmacol., 183, 55 1990); Zollinger-Ellison Syndrome (see Mozell, E., et al., Surg. Gynec. Obstet., 170, 476–484, 1990); hypersecretory diarrhea related to AIDS and other conditions (due to AIDS, see Cello, J. P., et al., Gastroenterology, 98, No. 5, Part 2, Suppl., A163 1990; due to elevated gastrin-releasing peptide, see Alhindawi, R., et al., Can. J. Surg., 33, 139–142, 1990; secondary to intestinal graft vs. host disease, see Bianco J. A., et al., Transplantation, 49, 1194–1195, 1990; diarrhea associated with chemotherapy, see Petrelli, N., et al., Proc. Amer. Soc. Clin. Oncol., Vol. 10, P 138, Abstr. No. 417 1991); irritable bowel syndrome (see O'Donnell, L. J. D., et al., Aliment. Pharmacol. Therap., Vol. 4., 177–181, 1990); pancreatitis (see Tulassay, Z., et al., Gastroenterology, 98, No. 5, Part 2, Suppl., A238, 1990); Crohn's Disease (see Fedorak, R. N., et al., Can. J. Gastroenterology, 3, No. 2, 53–57, 1989); systemic sclerosis (see Soudah, H., et al., Gastroenterology, 98, No. 5, Part 2, Suppl., A129, 1990); thyroid cancer (see Modigliani, E., et al., Ann., Endocr. (Paris), 50, 483–488, 1989); psoriasis (see Camisa, C., et al., Cleveland Clinic J. Med., 57, No. 1, 71–76, 1990); hypotension (see Hoeldtke, R. D., et al., Arch. Phys. Med. Rehabil., 69, 895–898, 1988 and Kooner, J. S., et al., Brit. J. Clin. Pharmacol., 28, 735P–736P, 1989); panic attacks (see Abelson, J. L., et al., Clin. Psychopharmacol., 10, 128–132, 1990); sclerodoma (see Soudah, H., et al., Clin. Res., Vol. 39, p. 303A, 1991); small bowel obstruction (see Nott, D. M., et al., Brit. J. Surg., Vol. 77, p. A691, 1990); gastroesophageal reflux (see Branch, M. S., et al., Gastroenterology, Vol. 100, No. 5, Part 2 Suppl., p. A425, 1991); duodenogastric reflux (see Hasler, W., et al., Gastroenterology, Vol. 100, No. 5, Part 2, Suppl., p. A448, 1991); Graves' Disease (see Chang, T. C., et al., Brit. Med. J., 304, p. 158, 1992); polycystic ovary disease (see Prelevic, G. M., et al., Metabolism Clinical and Experimental, 41, Suppl. 2, pp 76–79, 1992); upper gastrointestinal bleeding (see Jenkins, S. A., et al., Gut., 33, pp. 404–407, 1992 and Arrigoni, A., et al., American Journal of Gastroenterology, 87, p. 1311, (abs. 275), 1992); pancreatic pseudocysts and ascites (see Hartley, J. E., et al., J. Roy. Soc. Med., 85, pp. 107–108, 1992); leukemia (see Santini, et al., 78, (Suppl. 1), p. 429A (Abs. 1708), 1991); meningioma (see Koper, J. W., et al., J. Clin. Endocr. Metab., 74, pp. 543–547, 1992); and cancer cachexia (see Bartlett, D. L., et al., Surg. Forum., 42, pp. 14–16, 1991). The contents of the foregoing references are incorporated herein by reference.

Surprisingly, the Applicant has now discovered that lanreotide itself was particularly useful in treating the conditions, disorders and disease noted hereinabove.

The usefulness of lanreotide in the various disclosed new medical uses can be better understood through the results of tests relating to the treatment of upper gastrointestinal bleeding.

Lanreotide or a pharmaceutically-acceptable salt thereof can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 25 µg/kg/day to 100 mg/kg/day of body weight daily are administered as a single dose or divided into multiple doses to humans and other animals, e.g., mammals, to obtain the desired therapeutic effect.

A preferred general dosage range is 250 µg/kg/day to 5.0 mg/kg/day of body weight daily which can be administered as a single dose or divided into multiple doses.

Further, Lanreotide can be administered in a sustained release composition such as those described in the following patents. Among those formulations, 14-day or 28-day slow release formulations will be preferred. U.S. Pat. No. 5,672,659 teaches sustained release compositions comprising Lanreotide and a polyester. U.S. Pat. No. 5,595,760 teaches sustained release compositions comprising Lanreotide in a gelable form. U.S. application Ser. No. 08/929,363 filed Sep. 9, 1997, teaches polymeric sustained release compositions comprising Lanreotide and chitosan. U.S. application Ser. No. 08/740,778 filed Nov. 1, 1996, teaches sustained release compositions comprising Lanreotide and cyclodextrin. U.S. application Ser. No. 09/015,394 filed Jan. 29, 1998, teaches absorbable sustained release compositions of Lanreotide. The contents of the foregoing patents and applications are incorporated herein by reference.

The use of immediate or of sustained release compositions depends on the type of indications aimed at. If the indication consists of an acute or over-acute disorder, a treatment with an immediate form will be preferred over the same with a prolonged release composition. On the contrary, for preventive or long-term treatments, a prolonged release composition will generally be preferred.

Typically, to the indication upper gastrointestinal bleeding will correspond an acute or over-acute treatment with a dosage of 80 to 120 μg/day per person during approximately 5 days. After endoscopical treatment, preventive treatment against recurrence can be performed using lanreotide sustained release forms as an adjuvant to usual treatments; for this type of treatment, 14-day sustained release forms with a total dosage of approximately 30 mg lanreotide or 28-day lanreotide forms can be used.

For other indications than upper gastrointestinal bleeding, which correspond rather long term treatments, 14-day sustained release forms with a total dosage of approximately 30 mg lanreotide or 28-day lanreotide forms will be adequate.

What is claimed is:

1. A method of treating a disease or condition which comprises administering to a patient in need thereof an effective amount of the compound H-β-D-Nal-Cys-Tyr-D-Trp-Lys-Val-Cys-Thr-$NH_2$, where the two Cysteines are bonded by a disulfide bond, or a pharmaceutically acceptable salt thereof, wherein the disease or condition is selected from the group consisting of systemic sclerosis, pancreatic pseudocysts, pancreatic ascites, VIPoma, nesidoblastosis, hyperinsulinism, gastrinoma, Zollinger-Ellison Syndrome, hypersecretory diarrhea, scleroderma, irritable bowel syndrome, upper gastrointestinal bleeding, postprandial portal venous hypertension, complications of portal hypertension, small bowel obstruction, duodenogastric reflux, Cushing's Syndrome, gonadotropinoma, hyperparathyroidism, diabetic neuropathy, macular degeneration, hypercalcemia of malignancy, Paget's disease, meningioma, cancer cachexia, psoriasis, hypotension and panic attacks.

2. A method according to claim 1 wherein the acetate salt of H-β-D-Nal-Cys-Tyr-D-Trp-Lys-Val-Cys-Thr-$NH_2$ is administered.

3. A method according to claim 2 wherein the disease or condition is selected from the group consisting of VIPoma, nesidoblastosis, hyperinsulinism, gastrinoma, hypersecretory diarrhea, irritable bowel syndrome, upper gastrointestinal bleeding, postprandial portal venous hypertension, especially in cirrhotic patients, complications of portal hypertension, small bowel obstruction, diabetic neuropathy, meningioma and cancer cachexia.

4. A method according to claim 3 wherein the disease or condition treated is selected from the group consisting of VIPoma, nesidoblastosis, hypersecretory diarrhea, irritable bowel syndrome, small bowel obstruction and diabetic neuropathy.

* * * * *